(12) United States Patent
Ruas Da Silva et al.

(10) Patent No.: US 8,017,650 B2
(45) Date of Patent: Sep. 13, 2011

(54) 2,3,4,5-TETRAHYDROXY-6-SULFOOXY HEXANOIC ACID, PHARMACEUTICALLY ACCEPTABLE SALTS AND EQUILIBRIUM FORMS THEREOF, PROCESSES FOR THEIR PREPARATION, PHARMACEUTICAL COMPOSITIONS COMPRISING SUCH COMPOUNDS AND THEIR MEDICAL USE

(75) Inventors: Jorge Ruas Da Silva, Prior Velho (PT); Ana Maria Staack Reis Machado, Lisboa (PT); Joaquim Alberto Barros Pereira, Odivelas (PT); Joao Carlos Ramos Damil, Ermegeira (PT); Carlos Alberto Casimiro Caixado, Domingos Da Rana (PT); Augusto Eugenio Pardal Filipe, Lisboa (PT)

(73) Assignees: Jorge Ruas Da Silva, Sintra (PT); Maria do Carmo Neves Da Silva Ruas Da Silva, Sintra (PT); Miguel Ruas Da Silva, Sintra (PT); Jono Pedro Silva Serra, Sintra (PT)

( * ) Notice: Subject to any disclaimer, the term of this patent is extended or adjusted under 35 U.S.C. 154(b) by 547 days.

(21) Appl. No.: 12/093,785

(22) PCT Filed: Nov. 15, 2006

(86) PCT No.: PCT/IB2006/054278
§ 371 (c)(1),
(2), (4) Date: May 15, 2008

(87) PCT Pub. No.: WO2007/057849
PCT Pub. Date: May 24, 2007

(65) Prior Publication Data
US 2008/0279808 A1  Nov. 13, 2008

(30) Foreign Application Priority Data
Nov. 15, 2005  (PT) .......................... 103385

(51) Int. Cl.
*A61K 31/255* (2006.01)
*C07C 305/10* (2006.01)
(52) U.S. Cl. .............................. 514/517; 558/32; 558/34
(58) Field of Classification Search .................. 514/517; 558/32, 34
See application file for complete search history.

(56) References Cited

U.S. PATENT DOCUMENTS
| 6,455,573 | B1 | 9/2002 | Pinto et al. |
| 7,056,942 | B2 * | 6/2006 | Hildesheim et al. .......... 514/411 |
| 2003/0191104 | A1 | 10/2003 | Pinto et al. |
| 2007/0037870 | A1 | 2/2007 | Asada et al. |

FOREIGN PATENT DOCUMENTS
| CA | 2 522 793 A1 | 11/2004 |
| WO | 01/49674 A2 | 7/2001 |

OTHER PUBLICATIONS

J.W. Fitzgerald, et al. "Sulphur Utilization during Growth of *Pseudomonas fluorescens* on Potassium D-Glucose 6-0-Sulphate", Biochemical Journal, 1971, vol. 121, No. 3, pp. 521-528.
A.G. Lloyd, et al., "Observations on the Products Obtained After the Enzymic Oxidation of D-Glucose 6-O-Sulphate", Biochemical Journal, 1965, vol. 97, No. 3, p. 43P.
A.G. Lloyd et al., "Chemical Synthesis of Hexose and Hexosamine Sulphates", Jan. 10, 1959, vol. 183, No. 4654, pp. 109-110.
H.C. Reitz, et al. "Action of Sulfating Agents on Proteins and Model Substances. I. Concentrated Sulfuric Acid", Journal of the American Chemical Society, Jun. 1946, vol. 68, No. 6, pp. 1024-1031.
H.E. Fierz-David et al., "Nitroglycerinschwefelsauren und ihre Bedeutung im Nitroglycerinprozess", Mar. 15, 1949, vol. 32, No. 2, pp. 349-355.

* cited by examiner

*Primary Examiner* — Joseph Kosack
(74) *Attorney, Agent, or Firm* — Sughrue Mion, PLLC

(57) ABSTRACT

The invention relates to novel compounds of general formula I wherein M represents hydrogen, or a metallic cation, preferably an alkaline metal, or alkaline-earth metal, and n is equal to 1, 2 or 3. The present invention also comprises compounds of general formula I in their equilibrium forms, including lactonic forms, their enantiomers in pure form, or in an enriched form in one of the optical isomers, racemic mixtures, diastereomers and solvates thereof. The present invention further relates to processes for the preparation of compounds of general formula I, to pharmaceutical compositions comprising compounds of general formula I as only active ingredient, or in association with other active ingredients. Another aspect of the invention is the use of compounds of general formula I for the treatment of dyslipidemia, associated, or not, to other metabolic disorders, such as glucose intolerance syndrome and type 1 or 2 diabetes mellitus, by means of isolated administration or combined with other substances.

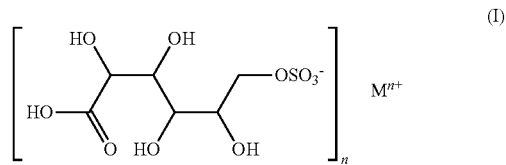

19 Claims, 1 Drawing Sheet

2,3,4,5-TETRAHYDROXY-6-SULFOOXY HEXANOIC ACID, PHARMACEUTICALLY ACCEPTABLE SALTS AND EQUILIBRIUM FORMS THEREOF, PROCESSES FOR THEIR PREPARATION, PHARMACEUTICAL COMPOSITIONS COMPRISING SUCH COMPOUNDS AND THEIR MEDICAL USE

FIELD OF THE INVENTION

The invention relates to novel compounds of general formula I

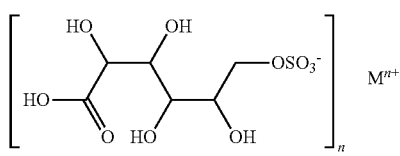
(I)

wherein M represents hydrogen, or a metallic cation, preferably an alkaline metal, or alkaline-earth metal, and n is equal to 1, 2 or 3. The present invention comprises also compounds of general formula I in their equilibrium forms, including lactonic forms, their enantiomers in pure form, or in an enriched form in one of the optical isomers, racemic mixtures, diastereomers and solvates thereof. The present invention further relates to processes for the preparation of compounds of general formula I, to pharmaceutical compositions comprising compounds of general formula I as only active ingredient, or in association with other active ingredients. Another aspect of the invention is the use of compounds of general formula I for the treatment of dyslipidemias, associated, or not, to other metabolic disorders, such as glucose intolerance syndrome and type 1 or 2 diabetes mellitus, by means of isolated administration or combined with other substances.

BACKGROUND OF THE INVENTION

For some decades, it has become evident that dyslipidemias are a major risk factor for the occurrence of cardiovascular diseases. Epidemiological studies carried out on human subjects made evident that a high level of LDL-C (low-density lipoprotein cholesterol) associated to a reduced level of HDL-C (high-density lipoprotein cholesterol) induce early atherosclerosis. On the other hand, several studies showed that the risk of coronary heart disease (CHD) can be reduced through hypocholesterolemic therapy. Framigham Heart Study, Multiple Risk Factor Intervention (MRFIT) and Lipid Research Clinics (LRC) found a direct relation between the serum concentration of LDL-C and the event rates in patients (male and female) with acute coronary without CHD history. Many studies showed that the risk of coronary diseases can be reduced due to hypolipemiant therapy. Until 1987, therapeutic strategies directed to lipid reduction were essentially limited to a diet poor in saturated fats and bile acid sequestrants (cholestyramine and colestipol), nicotinic acid (niacin), fibrates and probucol. Unfortunately, all these treatments have limited efficacy or tolerability, or both. Only after the appearance of HMG-CoA reductase inhibitors, such as lovastatin, pravastatin, simvastatin, mevastatin, atorvastatin, derivates and analogous thereof, medicals were able to obtain comparatively high reductions of cholesterol in plasma with very few adverse effects.

The administration of these compounds is associated to a reduction of mortality rate associated to coronary heart disease, and the risk of acute myocardial infarction, coronary revascularization procedures, cerebrovascular accident and peripheric vascular disease. The most frequently reported adverse effects are of muscular (myopathy) and hepatic (increase of hepatic enzymes) nature.

The HMG-CoA reductase inhibitors are indicated for dyslipidemia patients, essentially with LDL-C increase, when diet turns out to be insufficient for controlling the disorder. Patients with additional risk factors, like coronary heart disease or equivalents, diabetes mellitus and risk factors for coronary heart disease must be treated timely and intensively. In these circumstances, the object to be attained for LDL-C serum concentration (<100 mg/dl) requires higher doses of HMG-CoA inhibitors and/or association with other compounds.

This therapeutic area has been object of intense investigation and novel hypolipemiant agents are being studied.

The present invention discloses novel compounds useful for the treatment of hypocholesterolemia and atherosclerosis, a preparation process thereof and pharmaceutical compositions containing them.

The preparation of inorganic esters through the attack of an inorganic acid to an alcohol is known for a long time (see e.g. "Advanced Organic Chemistry, Reaction Mechanisms and Structure" $4^{th}$ edition, Jerry March, Wiley Interscience 1992). Namely, this reaction is used for the industrial production of detergents and cleaning agents, when fatty alcohols are made to react with sulphuric acid and subsequently converted into salts. However, these compounds are structurally different from the compounds of the present invention. In the prior state of art, no reference to general formula I was found, neither to processes for their preparation, or attempts for their synthesis and, as a result, no reference to possible industrial applications was found. The reaction using as substrate d-1-gluconic acid, or the racemic mixture, salts or lactones thereof for providing the corresponding monosulfates is new.

DETAILED DESCRIPTION OF THE INVENTION

Figure 1:
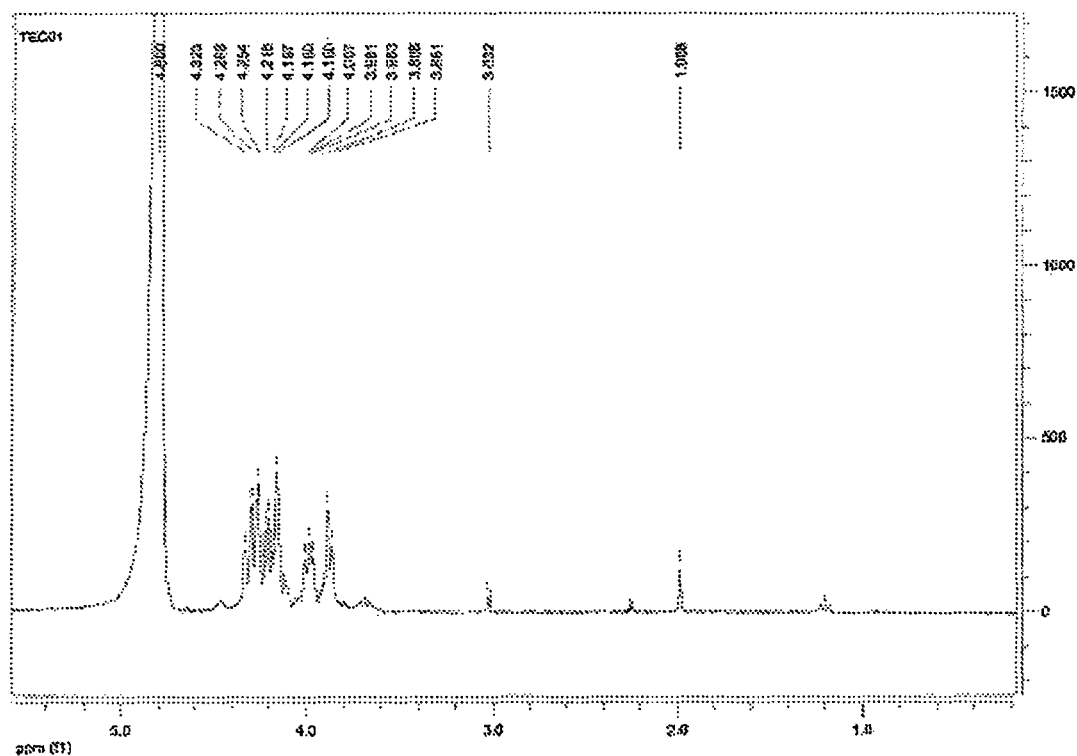
FIG. 1 illustrates a $^1$H-RMN spectrum in $D_2O$ (300 MHz) of 2,3,4,5-tetrahydroxy-6-sulfooxy hexanoic acid calcium salt.

In one aspect, the present invention refers to novel compounds of general formula I

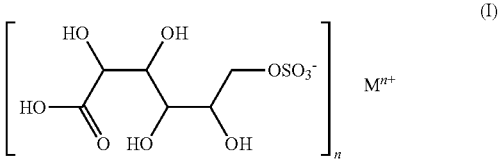
(I)

wherein M represents hydrogen, or a metallic cation, preferably an alkaline metal, or alkaline-earth metal, and n is equal to 1, 2 or 3. The present invention comprises also compounds of general formula I in their equilibrium forms, including lactonic forms, their enantiomers in pure form, or in an enriched form in one of the optical isomers, racemic mixtures, diastereomers and solvates thereof. The present invention further relates to processes for the preparation of compounds of general formula I, to pharmaceutical compositions comprising compounds of general formula I as only active ingredient, or in association with other active ingredients, and their use for the treatment of hypocholesterolemia and atherosclerosis.

It could be expected that monosulfate esters of compounds with polyalcoholic functions using sulphuric acid would not be interesting for synthetic purposes, due to the formation of mixtures comprising olefinic monosulfate esters, saturated and unsaturated polysulfated esters and polyhydroxyalcohols dehydration products. Despite the low yield, it was, surprisingly, found that the reaction between the d-1-gluconic acid, or racemic mixture, of its lactone, or salts thereof, in the absence or presence of an organic base, or aminoacid, originated the products of general formula I, with a low contamination of secondary dehydration products and other sulfates.

In another aspect, the present invention discloses processes for the production of compounds of general formula I. These processes comprise the cooling of an aqueous solution of 50% d-1-gluconic acid, or racemic mixture, or lactone thereof in an ice bath and the slow addition of sulphuric acid, keeping the temperature below 40° C. It is also possible to add an organic base, or an aminoacid, such as glycine, dimethylglycine, alanine, serine, cysteine, methanolamine, ethanolamine, or analogues thereof, preferably dimethylglycine, to an aqueous solution of 50% d-1-gluconic acid, or racemic mixture, or lactone thereof and stirring the mixture until complete dissolution, at a temperature between 30-70° C. The mixture is placed in an ice bath and concentrated sulphuric acid is slowly added, keeping the temperature below 40° C. The mixture is stirred further for 3 hours at 40° C., or at a slightly lower temperature. The water is distilled off under vacuum to a solids content of 75-78% and the reaction mixture is allowed to stand overnight at 40° C. The water is, once again, distilled off under vacuum until a solids content of 81-82%. The mixture is neutralized by adding, slowly under stirring while cooling, an excess amount of an aqueous suspension of a base, such as alkaline metal hydroxides, alkaline metal carbonates, alkaline-earth metal hydroxides, alkaline-earth metal carbonates, until a stable pH in the range of 4.5-9.0 is reached. The sulfates are filtered off and the precipitate is washed with water. The washings and the filtrate are combined and crude 2,3,4,5-tetrahydroxy-6-sulfooxy hexanoic acid salt precipitates by addition of an precipitation agent, such as a lower alcohol, preferably methanol, or ethanol. Lower alcohol means an alcohol with 1 to 4 carbon atoms of linear or branched chain, such as methanol, ethanol, isopropanol, butanol. The precipitate is filtered off and if desired, placed in a vacuum oven to dry. The conversion of 2,3,4,5-tetrahydroxy-6-sulfooxy hexanoic acid salt in the acid is carried out by the usual processes, well known to those skilled the art.

The crude reaction product contains, among other substances, the unreacted gluconic acid in salt form and the unconverted organic base, or aminoacid, when used in the reaction.

It is also an aspect of the invention the purification of 2,3,4,5-tetrahydroxy-6-sulfooxy hexanoic acid salt by nanofiltration. This technology is a pressure driven process for separating larger size solutes from aqueous solutions through a semi-permeable membrane. The pressure range used is typically within the range of 3.45 kPA-31.04 kPa. This process is carried out by passing a flow of solution through the membrane under pressure. Therefore, the driving force of the separation process is the pressure difference between the feed (retentate) and the filtrate (permeate) at the membrane separation surface. The membrane rejection is influenced by the size, structure and charge of the components in solution. Water and monovalent ions pass freely through the membrane, multivalent salts are retained. Due to the logarithmic decrease of the permeate flow rate, when the concentration increases, it is necessary to dilute the retentate with demineralised water and to run the nanofiltration process again. By applying this so called diafiltration step, it is possible to achieve a higher concentration in the desired products. In the present invention, when the compound of general formula I is in the form of a monovalent salt, the nanofiltration step is used for separating the organic base, or aminoacid, from the reaction mixture, when used. Choosing a membrane with an adequate molecular weight cut-off value it is possible to recover the organic base, or the aminoacid, in the permeate and reuse it in the chemical reaction. Preferably, the nanofiltration process is used when the compounds of general formula I are in the form of multivalent salts and, more preferably, in the form of divalent salts, because not only the organic base, or the aminoacid, is separated from the reaction mixture, but also the unconverted gluconic acid in salt form is partially extracted, enabling to concentrate further desired compound in the retentate. An additional increase of concentration grade can be obtained, if desired, through the addition of a monovalent salt, such as for example sodium sulfate. An increased amount of gluconate anion will pass through the membrane, for example, under the form of sodium gluconate. Therefore, it will be possible to increase the amount of compound one wishes to concentrate in the retentate. The nanofiltration is carried out at a temperature within the range of 20° C.-40° C. Examples 2-4 explain in a more detailed way the nanofiltration step of the present invention. Finally, the product is submitted to a preparative high-pressure liquid chromatography (PHPLC), using as eluent acetic acid:water:1-butanol (25:25:50), using as stationary phase silica gel, or hydrophilic interaction chromatography (HILIC).

In another aspect, the present invention provides pharmaceutical compositions comprising compounds of general formula I as only active ingredient or in association with other active ingredients. The compounds of general formula I can be combined, for example, with at least one normolipidemic selected from inhibitors of HMG-CoA reductase, agonists of the peroxisome proliferator activated receptors (PPAR) or ion exchange resins.

As examples of HMG-CoA reductase inhibitors are indicated Lovastatin, Atorvastatin, Pravastatin, Simvastatin, Rosuvastatin, Pitavastatin, Mevastatin or Fluvastatin.

The PPAR agonists can be of subtype PPARα, PPARγ or double PPARα and PPARγ, being selected from the Bezafibrate, Ciprofibrate, Etofibrate, Fenofibrate, Gemfibrozil, Troglitazone, Rosiglitazone, Pioglitazone or Muraglitazar.

From the group of ion exchange resins can be selected Colestipol or Colestiramine. The pharmaceutical composition can be presented under the form of tablets, granules, coated tablets or sugar film coated granules or with an enteric coating, capsules, suspension, solution, emulsion, etc. These compositions can be prepared as medication for oral, parenteral, rectal, transdermal, buccal or nasal administration. They may comprise the addition to the active ingredient of one or several compounds selected from adequate vehicles, diluents, fillers, solvents, lubricants, aggregants, disintegrants, preservatives, emulsifiers, etc.

Another aspect of the invention is the use of compounds of general formula I for the treatment of dyslipidemias, associated or not to other metabolic disorders, such as the glucose intolerance syndrome and type 1 or 2 diabetes mellitus, by means of isolated administration or combined with other active substances, as the ones mentioned above. The invention is subsequently described in more detail through the following non-limiting examples of the scope of the present invention

EXAMPLE 1

Preparation of 2,3,4,5-tetrahydroxy-6-sulfooxy hexanoic acid calcium salt

A solution of 643.2 g dimethylglycine hydrochloride and 1224 ml of an 50% aqueous solution of d-gluconic acid solution are stirred in a 3 l flask until total dissolution at a temperature of 40° C. The mixture is placed in an ice bath and 385 ml concentrated sulphuric acid are slowly added, keeping the temperature below 40° C. The mixture is stirred further for 3 hours at 40° C., or at a temperature slightly below. The water is distilled off under vacuum to a solids content of about 75-78% and the reaction mixture is allowed to stand at 40° C. overnight. The water is distilled off under vacuum again to a solids content of 81-82%. The mixture is neutralized by adding, under stirring, an excess amount of calcium hydroxide until reaching a stable pH value in the range of 4.5-9.0. The calcium sulfate is filtered off and the precipitate is washed with water. The washings and the filtrate are combined and crude 2,3,4,5-tetrahydroxy-6-sulfooxy hexanoic acid calcium salt precipitates by the addition of ca. 9 l of ethanol. The precipitate is filtered off and, if desired, the resulting product is placed in a vacuum oven to dry.

EXAMPLE 2

Nanofiltration of the Crude Reaction Product

The nanofiltration was carried out with a Desal-5 thin film membrane with a molecular weight cut-off of 160-300 Daltons for uncharged organic molecules.
Quantity of reaction mixture for nanofiltration: 1.5 kg
Concentration of reaction mixture in the retentate vessel at beginning of operation: 100 µl
Osmotic pressure: 15 bar
Column temperature during nanofiltration: 20-25° C.
Mass percentage of dimethylglycine in the reaction mixture: 14.88%
Mass percentage of calcium gluconate in the reaction mixture: 21.14%
Mass percentage of 2,3,4,5-tetrahydroxy-6-sulfooxy hexanoic acid calcium salt in the reaction mixture: 13.27%
Diafiltration water: 180 l
Mass percentage of dimethylglycine after nanofiltration: 0%
Mass percentage of calcium gluconate after nanofiltration: 22%
Mass percentage of 2,3,4,5-tetrahydroxy-6-sulfooxy hexanoic acid calcium salt after nanofiltration: 22%

EXAMPLE 3

The nanofiltered product obtained according to the proceeding described in Example 2 was subjected to three further nanofiltration processes according to Example 2. The product composition obtained after a total of four nanofiltration processes is as follows:

Mass percentage of dimethylglycine after nanofiltration: 0%
Mass percentage of calcium gluconate after nanofiltration: 26%
Mass percentage of 2,3,4,5-tetrahydroxy-6-sulfooxy hexanoic acid calcium salt after nanofiltration: 50%

EXAMPLE 4

Nanofiltration of Crude Reaction Product

The nanofiltration was carried out with a Desal-5 thin film membrane with a molecular weight cut-off of 160-300 Daltons for uncharged organic molecules.
Quantity of the reaction mixture for nanofiltration: 1.5 kg
Concentration of reaction mixture in the retentate vessel at beginning of operation: 100 g/l
Quantity of sodium sulfate added to the reaction mixture: 99 g
Osmotic pressure: 15 bar
Column temperature during nanofiltration: 20-25° C.
Mass percentage of dimethylglycine in the reaction mixture: 14.88%
Mass percentage of calcium gluconate in the reaction mixture: 21.14%
Mass percentage of 2,3,4,5-tetrahydroxy-6-sulfooxy hexanoic acid calcium salt in the reaction mixture: 13.27%
Diafiltration water: 180 l
Mass percentage of dimethylglycine after nanofiltration: 0%
Mass percentage of calcium gluconate after nanofiltration: 22%
Mass percentage of 2,3,4,5-tetrahydroxy-6-sulfooxy hexanoic acid calcium salt after nanofiltration: 40%

EXAMPLE 5

Figure 2:
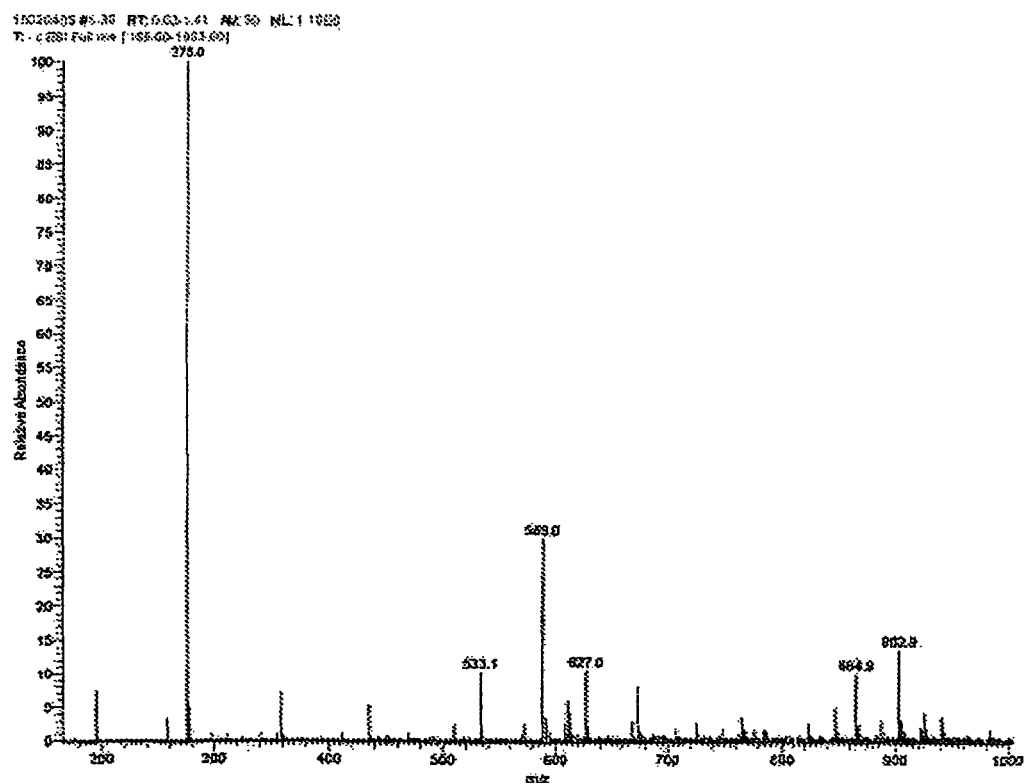
FIG. 2 illustrates an average mass spectrum of 2,3,4,5-tetrahydroxy-6-sulfooxy hexanoic acid calcium salt. Electrospray ionization (ESI) source with a source voltage of 4.5 kV, a capillary voltage of −24 V and an ion trap were used.

The product obtained after the nanofiltration step is submitted to a preparative high-pressure liquid chromatography, using as eluent acetic acid:water:1-butanol (25:25:50), and using as stationary phase silica gel. 2,3,4,5-tetrahydroxy-6-sulfooxy hexanoic acid calcium salt in the form of white powder is obtained. In FIGS. 1 and 2 are presented, respectively, the $^1$H-RMN in $D_2O$ (300 MHz) and mass (ESI) spectra.

EXAMPLE 6

A clinical test with a duration of 12 weeks was carried out on approximately 60 patients with hypocholesterolemia and indication for pharmacological hypolipemiant therapy with inhibitors of hydroxymethylglutaryl coenzyme A reductase (HMG-CoA reductase), according to the criteria of the National Cholesterol Education Program—Adult Treatment Panel III (NCEP-ATP III). The clinical test evaluated, firstly, the efficiency of an experimental intervention consisting in the combined treatment of a compound of the group of inhibitors of HMG-CoA reductase and a compound of general formula I (Group II), comparatively to the isolated treatment with a compound of the group of inhibitors of HMG-CoA reductase (Group I). The primarily variable was the average variation between the final values and the basal values of LDL-C (low-density lipoprotein-cholesterol) plasma concentration. After the experimental intervention, in Group II was observed an average reduction of 54.30 mg/dl, while the reduction in Group II was of 34.30 mg/dl. Next, the same comparison was realized for the average variation of total cholesterol plasma concentration (−67.20 mg/dl versus −50.25 mg/dl), non-HDL (high density lipoprotein) cholesterol (−95.80 mg/dl versus −54.50 mg/dl) and triglycerides (−151 mg/dl versus −123.0 mg/dl). Referring to the average variation of C-HDL (cholesterol-high density lipoprotein) plasma concentration, its increase is associated to the reduction of cardiovascular risk and the variation observed in the clinical test was of +8.67 mg/dl (Group II) versus +4.25 mg/dl (Group I). This way, the clinical test showed that the combination of a compound of HMG-CoA reductase inhibitor group and of a compound of general formula I is more effective in the treatment of dyslipidemias than the isolated administration of a compound of HMG-CoA reductase inhibitor group.

In this clinical test were included patients suffering from metabolic disorders, such as glucose intolerance and type 1 or 2 diabetes mellitus.

EXAMPLE 7

A clinical test on patients suffering from diabetes mellitus and from dyslipidemia associated to diabetes mellitus was realized, with indication for pharmacological hypolipemiant therapy with HMG-CoA reductase inhibitors, according to the criteria of the National Cholesterol Education Program—Adult Treatment Panel III (NCEP-ATP III). The clinical test evaluated, firstly, the efficiency of combined treatment of a compound of the statin group and a compound of general formula I (Group II), comparatively to the isolated treatment with a compound of the statin group (Group I), after a treatment period of 12 weeks, under LDL-C plasma concentration. Next, the same comparison was realized for the total cholesterol plasma concentration, HDL-C and triglycerides.

The invention claimed is:
1. Compounds of the general formula I

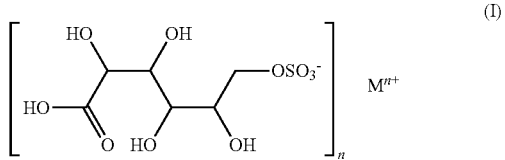

their enantiomers in pure form, or in an optically enriched form, racemic mixtures or diastereomers thereof, wherein M represents an alkaline metal, or alkaline-earth metal, excluding the barium salt or dipotassium salt, and n can be 1, 2, or 3.

2. Compounds of the general formula I according to claim 1, being 2,3,4,5-tetrahydroxy-6-sulfooxy-hexanoic acid calcium salt, their enantiomers in pure form, or in an enriched form in one of the optical isomers, racemic mixtures or diastereomers thereof.

3. Process for the preparation of compounds of general formula I according to claim 1, their enantiomers in pure form, or in an optically enriched form, racemic mixtures or diastereomers thereof, wherein the d,l-gluconic acid or racemic mixture, or salts thereof react with sulphuric acid in the presence or absence of an organic base, or amino acid.

4. Process for the preparation of compounds of general formula I according to claim 3, wherein the organic base or the amino acid is glycine, dimethylglycine, alanine, serine, cystine, methanolamine, ethanolamine or analogues thereof.

5. Process for the preparation of compounds of general formula I according to claim 3, wherein the reaction is carried out at temperatures within the range of 30-70° C.

6. Process for the preparation of compounds of general formula I according to claim 3, wherein the reaction mixture is concentrated and subsequently neutralized by addition of an aqueous suspension of alkaline metal hydroxides, alkaline metal carbonates, alkaline-earth metal hydroxides, alkaline-earth metal carbonates or mixtures thereof until a stable pH in the range of 4.5-9.0 is reached.

7. Process for the preparation of compounds of general formula I according to claim 3, wherein the crude product is precipitated by the addition of a precipitation agent comprised of methanol, ethanol, isopropanol or butanol.

8. Process for the preparation of compounds of general formula I according to claim 3, comprising furthermore a nanofiltration step after chemical reaction according to claim 3 for eliminating the organic base or amino acid, when used, and for concentrating the reaction mixture in the desired product.

9. Process for the preparation of compounds of general formula I according to claim 3, comprising a final purification by high-pressure liquid chromatography (HPLC).

10. Process for the preparation of compounds of general formula I according to claim 9, wherein the stationary phase used in the high-pressure liquid chromatography is silica gel, or a stationary phase hydrophilic interaction liquid chromatography stationary phase.

11. Pharmaceutical composition comprising compounds of general formula I according to claim 1, their enantiomers in pure form, or in an optically enriched form, racemic mixtures or diastereomers thereof, and one or more pharmaceutically acceptable vehicle substances.

12. Pharmaceutical composition comprising compounds of general formula I according to claim 1, their enantiomers in pure form, or in an optically enriched form, racemic mixtures or diastereomers thereof, in combination with at least one normolipidemic selected from HMG-CoA reductase inhibitors, PPAR agonists or ion exchange resins, and one or more pharmaceutically acceptable vehicle substances.

13. Pharmaceutical composition according to claim 12 comprising compounds of general formula I in combination with an HMG-CoA reductase, a PPAR agonists and an ion exchange resin, and one or more pharmaceutically acceptable vehicle substances.

14. Pharmaceutical composition according to claim 12, wherein the HMG-CoA reductase inhibitor is Lovastatin, Atorvastatin, Pravastatin, Simvastatin, Rosuvastatin, Pitavastatin, Mevastatin or Fluvastatin.

15. Pharmaceutical composition according to claim 12, wherein the PPAR agonist is Bezafibrate, Ciprofibrate, Etofibrate, Fenofibrate, Gemfibrozil, Troglitazone, Rosiglitazone, Pioglitazone or Muraglitazar.

16. Pharmaceutical composition according to claim 12, wherein the ion exchange resin is Colestipol or Colestiramine.

17. Method of treating dyslipidemias associated or not to other metabolic disorders comprised of glucose intolerance syndrome and type 1 or 2 diabetes mellitus comprising administering the compounds of general formula I according to claim 1, their enantiomers in pure form, or in an optically enriched form, racemic mixtures or diastereomers thereof to a subject in need thereof.

18. Method of treating dyslipidemias associated or not to other metabolic disorders comprised of glucose intolerance syndrome and type 1 or 2 diabetes mellitus comprising administering the compounds of general formula I according to claim 1, their enantiomers in pure form, or in an optically enriched form, racemic mixtures or diastereomers thereof, in combination with at least one normolipidemic selected from HMG-CoA reductase inhibitor, PPAR agonists or ion exchange resins, to a subject in need thereof.

19. Method of treating dyslipidemias associated or not to other metabolic disorders comprised of glucose intolerance syndrome and type 1 or 2 diabetes mellitus comprising administering the compounds of general formula I according to claim 1, their enantiomers in pure form, or in an optically enriched form, racemic mixtures or diastereomers thereof, in combination with an HMG-CoA reductase inhibitor, a PPAR agonist or an ion exchange resin, to a subject in need thereof.

* * * * *